United States Patent [19]
Fuller

[11] Patent Number: 5,830,642
[45] Date of Patent: Nov. 3, 1998

[54] ELECTROPHORESIS OF NUCLEIC ACID FRAGMENTS

[75] Inventor: Carl W. Fuller, Cleveland Heights, Ohio

[73] Assignee: Amersham Life Science, Inc., Cleveland, Ohio

[21] Appl. No.: 928,852

[22] Filed: Aug. 10, 1992

Related U.S. Application Data

[63] Continuation-in-part of Ser. No. 862,734, Apr. 3, 1992.

[51] Int. Cl.$^6$ .............................. C12Q 1/68; C12P 19/34; G01N 27/26
[52] U.S. Cl. ................................ 435/6; 435/91; 435/91.5; 435/183; 436/94; 935/77; 204/450; 204/456
[58] Field of Search ................................ 435/6, 91, 810, 435/183, 91.5; 436/94; 204/180.1, 182.8, 450, 456, 91.2; 252/182.12; 935/77

[56] References Cited

U.S. PATENT DOCUMENTS

| | | | |
|---|---|---|---|
| 4,795,699 | 1/1989 | Tabor | 435/5 |
| 4,844,786 | 7/1989 | Sugihara | 204/299 |
| 5,041,371 | 8/1991 | Cowan et al. | 435/91 X |
| 5,075,216 | 12/1991 | Innis | 435/6 |
| 5,314,809 | 5/1994 | Erlice | 435/91.2 |

FOREIGN PATENT DOCUMENTS

| | | |
|---|---|---|
| 9008839 | 8/1990 | WIPO . |

OTHER PUBLICATIONS

Thivierge, Bethany, Amplification: A Forum for PCR Users, 1989, Issue 2, pp. 9–10.
Perkei elmer Catalog (1992) pp. 5, 9, 11, 64 & 65.
Lantick et al DNA (1984) 3:413–419.
Wilson et al Genomics (1990) 6:626–634.
Stoll et al, Methods in Enzynology, Guide to Protein Purification, 1990 Academic Press, Inc, vol. 182, pp. 24–31.
Thangavelu et al Cytogenet Cell Genet 1991 58(1–4) 2154.
Hong, Bioscience (1982) 2:907–912.
Straus et al BioTechniques (Mar. 1991)10: 376–384.
U.S. Biochemical Catalog (1990) pp. 94, 115&116.
Schleif et al Practical Methods in Moleculer Biology, 1981 Springer–Verlag, new York, NY, pp. 114–119.
Pharmacia Catlog, pp. 120–123, 184.
Mamatis et al. Molecular Cloning: A Laboratory Manual, 1st Ed, 1982, Cold Spring Harbor Laboratory Press, NY, pp. 104–106.
Carninci et al., A simple discontinuous buffer system for increased resolution and speed in gel electrophoretic analysis of DNA sequencing, 18 Nucleic Acids Research 204, 1989.
Richards et al., Disc Electrophoresis of Ribonucleic Acid in Polyacrylamide Gels, 12 Anal. Biochem. 452, 1965.
Peacock et al., "Resolution of Multiple Ribonucleic Acid Species by Polyacrylamide Gel Electrophoresis", 6 Biochemistry 1818, 1967.
Ansorpe et al., "System for DNA sequencing with resolution of up to 600 base pairs", 9 J. Bioc. Biop. Meth. 33, 1984.
Brumley et al., "Rapid DNA sequencing by horizontal ultrathin gel electrophoresis", 19 Nucleic Acids Research 4121, 1991.
Wyckoff et al., "Polyacrylamide Gel Electrophoresis in sodium Dodecyl Sulfate–Containing Buffers Using Multiphasic Buffer Systems: Properties of the Stack, Valid $R_f$–Measurement, and Optimized Procedure", 78 Anal. Biochem. 459, 1977.
Fuller, "The Effect of Excess Glycerol on DNA Sequencing Gels", USB Comments (brochure).

*Primary Examiner*—Carla J. Myers
*Attorney, Agent, or Firm*—Lyon & Lyon LLP

[57] ABSTRACT

A method for electrophoresis of nucleic acid fragments present in the solution which contains an amount, e.g., 0.2% or more, of a reagent, e.g., glycerol, dithiolthreitol (DTT) and trehalose or other sugars, which interact to form a complex with borate or boric acid. The method includes applying the solution to an electrophoretic gel and electrophoresing those fragments into the gel in the presence of a buffer lacking boric acid, or a derivative thereof, which forms a chelate complex with the reagent and thereby causes distortion of electrophoresis of the fragments in a gel including such a buffer.

16 Claims, 6 Drawing Sheets

LOW STRINGENCY PRIMING

```
                              FALSE PRIMING                              PRINCIPLE PRIMING
                                 SITE                                         SITE
                                                   5' GCCTACGTTCACAGCTG
                                                      ||||||||||||||||||
5' GCCTACGTTTCACAGCTG                                 CCGGATGCAAGTGTCGACTATC
   ||||||||  ||||||||
   CCATACTCGATGCGTGTCGACACCCATTCCGGATGCAAGTGTCGACTATC
   TEMPLATE DNA
```

HIGH STRINGENCY PRIMING

```
                                                     PRINCIPLE PRIMING
                                                          SITE
                                                   5' GCCTACGTTCACAGCTG
                                                      ||||||||||||||||||
5' GCCTACGTTTCACAGCTG                                 CCGGATGCAAGTGTCGACTATC
   NO FALSE
   PRIMING
   CCATACTCGATGCGTGTCGACACCCATTCCGGATGCAAGTGTCGACTATC
   TEMPLATE DNA
```

ELECTROPHORESIS OF NUCLEIC ACID FRAGMENTS

This application is a continuation-in-part of Fuller, U.S. Ser. No. 07/862,734, filed Apr. 3, 1992 hereby incorporated by reference herein.

FIELD OF THE INVENTION

This invention relates to methods and kits for electrophoresis of nucleic acid fragments, particularly those methods and kits useful for electrophoresing nucleic acid fragments contained in a solution which includes glycerol.

BACKGROUND OF THE INVENTION

Fuller, 16 *Comments* 1989 reports that the presence of glycerol in a sample loaded on an electrophoretic gel may cause artifacts, such as distortion of nucleic acid fragments in DNA sequencing gels. The distortion is said to resemble a bulge in the sequencing gel, and renders the 400–600 nucleotide region of the gel unreadable. Fuller states that because of the distortion caused by the presence of glycerol, United States Biochemical Corporation supplies a sequencing enzyme, SEQUENASE Version 2.0 T7 DNA polymerase, at a high enough concentration so that no glycerol distortion occurs when the enzyme is diluted prior to use.

Carninci et al. 18 *Nucleic Acids Research* 204, 1989 describe a standard sequencing gel system using Tris/Borate/EDTA buffer (TBE). It also describes a discontinuous buffer system using Tris-sulphate and Tris-borate. The Tris-sulphate is used as a running gel buffer, and Tris-borate as a tank buffer.

Richards, et al., 12 *Analytical Biochemistry* 452, 1965 and Peacock and Dingman, 6 *Biochemistry* 1818, 1967 describe electrophoresis of ribonucleic acid in polyacrylamide gels and resolution of multiple RNA species by polyacrylamide gel electrophoresis. Richards, et al., describe use of Tris-HCl buffer as well as acetic, cacodylic, diethyl barbituric, and glycyl glycine buffers. Peacock and Dingman describe use of Tris-EDTA and boric acid buffers for electrophoresis. The RNA species are not provided in glycerol-containing samples.

Ansorge and Barker, 9 *J. Bioc. Biop. Meth.* 33, 1984 describe use of Tris/Tricine buffer and an ammediol system for electrophoresis of Maxam and Gilbert DNA sequencing products. Such products are provided in samples without glycerol.

Brumley and Smith, 19 *Nuc. Acid. Res.* 4121, 1991 describe use of a borate buffer for a sequencing gel.

SUMMARY OF THE INVENTION

The present invention concerns use of an electrophoretic buffer, for electrophoresis of nucleic acids, which does not form a chelate complex with glycerol or other reagents. Such complexes, e.g., between boric acid and glycerol, are described by Cotton and Wilkinson, *Advanced Inorganic Chemistry*, 1980, John Wiley & Sons, p. 298. Other such complexes may be formed between borate and various sugars, such as ethylene glycol, trehalose or dithiothreitol (DTT) which may be used as stabilizing agents for an enzyme (e.g., trehalose is used by Quadrant for stabilizing a dried enzyme preparation). The presence of such a complex within an electrophoretic gel causes distortion of negatively charged DNA molecules within the gel. The complex is negatively charged under electrophoretic gel conditions and migrates through the gel along with the negatively charged DNA. It is present in sufficient amount to overload the gel, causing distortion of adjacent DNA bands within the gel.

Applicant has discovered that substitution of a different weak acid for boric acid in an electrophoretic gel buffer eliminates gel distortion. The invention features a method for electrophoresis of nucleic acid fragments, such as those produced during DNA sequencing procedures, by use of a buffer which does not form a complex with glycerol or other reagents. This enables use of glycerol or the other reagents at high concentrations in DNA sequencing reactions or other reactions concerning nucleic acids. Such high concentrations are advantageous because they are more convenient and they increase the stability of the enzymes within a reaction mixture.

Thus, in the first aspect the invention features a method for electrophoresis of nucleic acid fragments present in the solution which contains an amount, e.g., 0.2% or more, of a reagent, e.g., glycerol, DTT, and trehalose or other sugars, which interacts to form a complex with borate or boric acid. Generally, boric acid may react with any 1,2-diol compound, and the stability of the product depends on the relative orientation of the alcohols. Thus, complexes with trans glycols are weaker than with cis glycols. Examples of such 1,2-diols (glycols) include ethylene glycol, propylene glycol, butylene glycol, threitol, erythritol, dithioerythritol, pinacol, ribose, mannitol, glucitol, ribitol, sorbitol, inositols, SPAN® and TWEEN® detergents, sorbose, ascorbic acid, FICOLL® polymer, dextran, and derivatives thereof. Various sugars will also react, including glyceraldehyde, erythrose, threose, arabinose, xylose, lyxose, allose, altrose, glucose, mannose, gulose, idose, galactose, talose, fructose, ribulose, xylulose, fucose, rhamnose, fructose, glycosides of these, sucrose and other oligosaccharides, polysaccharides, cellobiose, maltose, lactose, trehalose, gentiobiose, melibiose, cellulose, and starches. Amino-sugars, acylaminosugars and glycosides may also react. That is, any compound having a 1,2-diol moiety which reacts with borate to form an anionic chelate complex is best avoided in gel compositions and reagents run into a gel. The method includes applying the solution to an electrophoretic gel and electrophoresing those fragments into the gel in the presence of a buffer lacking boric acid, or a derivative thereof, which forms a chelate complex with the reagent and thereby causes distortion (i.e., makes reading of the DNA sequence more difficult than if there were no distortion) of electrophoresis of the fragments.

In preferred embodiments, the fragments are produced during an enzymatic DNA sequencing reaction; the gel is a DNA sequencing gel; the reaction is performed in the presence of the glycerol; and the acid portion of the buffer is selected from acetic acid, carbonic acid, glycine, serine, taurine, tricine, and bicine. The basic portion may be Tris or ammediol or any other equivalent buffer components.

In a related aspect, the invention features a kit for DNA sequencing which includes reagents, e.g., DNA polymerase, necessary for DNA sequencing, and an electrophoretic buffer selected from those described above. Most preferably, the polymerase is provided at a concentration in a glycerol-containing buffer which does not need dilution prior to use (e.g., within a microtitre well format). By not needing dilution is meant that the DNA polymerase can be used directly in a sequencing reaction without a step of dilution of the enzyme prior to addition to other components and in a volume that can be readily and accurately transferred by commonly available pipetting devices (2 µl of 50% glycerol solution).

Prior to this invention, SEQUENASE DNA polymerase and DELTS TAQ DNA polymerase were provided at high concentration (e.g., at 13 U/µl for SEQUENASE DNA polymerase and 32 U/µl for DELTA TAQ DNA polymerase) in a sequencing kit (in 50% glycerol) and the customer was forced to dilute it 8-fold (e.g., to 1.6 U/µl or 4 U/µl for SEQUENASE DNA polymerase and DELTA TAQ DNA polymerase, respectively) prior to use. This represents a compromise among convenience, stability and gel readability. When diluted in the labeling reaction mixture (without glycerol), SEQUENASE DNA polymerase remains stable only 10–15 minutes at room temperature in the first step of the sequencing reaction, but the reaction can be completed in 5 minutes and the gel distortion is acceptably small. The polymerase, however, is stable if diluted in the presence of glycerol.

The present invention eliminates the distortions on the gels, by using a new gel buffer in place of the traditional TBE buffer. The use of this new buffer provides the following advantages (other are exemplified below):

1. The SEQUENASE or DELTA TAQ DNA polymerase can be supplied pre-diluted in 50% glycerol, eliminating a tedious step in the sequencing protocol. It can simply be added directly from the kit vial in a convenient volume of 2 µl.
2. Enzyme dilution buffer is not required in a sequencing kit.
3. The enzyme can be much more stable in use, allowing more leeway (in time and temperature) in the manner the reactions are run. This allows easier dispensing of enzyme by slow automated equipment during use. There are distinct improvements in sequencing results with higher concentrations of glycerol, especially with double-stranded templates.
4. Contaminants in the template which may destabilize the enzyme are less troublesome.
5. The end user of a typical 100 test DNA sequencing kit will prefer receiving a vial containing 200 µl of enzyme over the current 25 µl. This way, it is possible to run just one reaction without wasting enzyme in dilution.
6. Elimination of the gel distortion caused by glycerol is particularly useful for procedures which make use of added restriction enzymes and gene 6 exonuclease, such as lambda DNA sequencing.
7. A microtiter-plate format sequencing kit can be more readily produced. The reagents (including enzyme) can be pre-dispensed in 96-well plates and used to sequence 1–12 templates simultaneously. Unused portions of the plate can be returned to the freezer for later use.
8. When sufficient glycerol is added to reactions run with SEQUENASE T7 DNA Polymerase, the termination reactions can be run at high temperature by pre-warming the termination reaction vials to 70° C. This high temperature may eliminate template secondary structure problems.

It is these advantages that make possible other aspects of the invention in which a thermolabile DNA polymerase (i.e., one which loses activity above about 37° C., e.g., T7 DNA polymerase, and Klenow) can be used in the labelling and/or termination steps of a DNA sequencing reaction at high temperatures of 37° C. and 60° C. respectively. Such sequencing procedures provide superior results to those previously obtained, as discussed below.

Other features and advantages of the invention will be apparent from the following description of the preferred embodiments thereof, and from the claims.

DESCRIPTION OF THE PREFERRED EMBODIMENTS

The drawings will first briefly be described.

Drawings

Gel Electrophoresis

Current methods for sequencing DNA rely on electrophoresis gels to resolve DNA fragments according to their size or molecular weight, Maxam and Gilbert, 65 *Methods in Enzymology* 499, 1980, Maxam and Gilbert, 74 *Proc. Nat. Acad. Sci. USA* 560, 1977, Sanger, et al., 74 *Proc. Nat. Acad. Sci. USA* 5463, 1977. A population of DNA fragments is prepared in such a way that all the fragments have a particular sequence at one end, and at the other end have generally only one (of the four possible) nucleotides. Thus, the presence of a fragment containing 50 nucleotides (in addition to a region known as a primer) in the population of adenosine-terminated fragments indicates that adenosine is present in the 50th position of the sequence.

High-resolution separation of DNA fragments by size is an essential component of a sequencing method. Sequencing gels are typically larger and thinner than other kinds of electrophoresis gel, so that high possible resolution is achieved, resulting in the determination of large numbers of bases in a single electrophoresis run. Gels typically resolve 150–300 nucleotides in a single run, but there have been reports of resolving 500 or more bases using particularly long gels, or special apparatus. Tabor and Richardson, 84 *Proc. Natl. Acad. Sci. USA* 4767, 1987, Sieminiak et al., 192 *Anal. Biochem.* 441, 1991.

Examples of sequencing gels now in use generally include 6–8% polyacrylamide crosslinked with N, N'-methylene bisacrylamide (20:1 acrylamide to bisacrylamide to bisacrylamide by weight), 7–8.3 M urea and TBE buffer (10.8 g tris (hydroxymethyl) aminomethane ("Tris"), 0.93 g disodium EDTA, and 5.5 g boric acid per liter of solution) to give final concentrations of 0.09 M Tris, 0.09 M boric acid and 0.0025 M EDTA. This buffer was first described by Peacock and Dingman in 6 *Biochemistry* 1818, 1967 for the separation of RNA species by polyacrylamide gel electrophoresis. The addition of urea to this buffer to denature the DNA was described by Maniatis, et al. in 14 *Biochemistry* 3787, 1975, and for sequencing DNA by Air, et al. in 108 *J. Mol. Biol.* 519, 1976.

The composition of sequencing gels has not changed significantly since 1976, although some workers use formamide, alternative crosslinkers, and reagents which bind the gel to glass.

The DNA Polymerase used for performing a sequencing reaction to form the desired DNA fragment preparations is stored in 50% glycerol to keep it stable at reaction temperatures or during storage at −20° C. It is difficult to accurately transfer volumes of less than 2 μl of 50% glycerol. Thus, it is necessary to dilute the DNA polymerase immediately prior to use, thereby diluting the glycerol to acceptable levels. Alternatively, the samples are purified by precipitation with ethanol prior to loading on the gel.

While these measures eliminate the gel-distortion problem, they are somewhat cumbersome, and time consuming. Thus, the present invention features a new gel formulation which tolerates glycerol in the sample. Since the polymerase can be maintained in high concentrations of glycerol at all times, potential problems which result from enzyme inactivation are eliminated.

When glycerol is applied to an ordinary TBE-buffered DNA sequencing gel, it complexes with boric acid and migrates through the gel. If the quantity of glycerol is large enough to overload the gel, it distorts the region of the gel in which it migrates. The degree of distortion depends on the amount of glycerol loaded and the size of the gel. When following the nominal protocol used for the SEQUENASE DNA sequencing kits, 10.7 μg of glycerol is loaded into each sequencing gel lane along with about 0.25 μg of DNA. This amount of glycerol does not normally interfere with DNA migration on the gel. If the enzyme is diluted in a buffer containing 50% glycerol, more than 85 μg of glycerol is present in the sample applied to the lane. This quantity is enough to severely distort the pattern of DNA band migration. Typical amounts of glycerol loaded on a sequencing gel are listed in Table 1.

TABLE 1

| Glycerol Concentration (%) | SEQUENASE Kits | TAQUENCE Kits | SEQUENASE Kit, no Enzyme Dilution | 96-well Kit as described |
|---|---|---|---|---|
| Enzyme | 50 | 50 | 50 | 50 |
| Diluted Enzyme | 6.25 | 6.25 | 50 | 50 |
| Labeling Reaction | 0.806 | 0.714 | 6.45 | 25.9 |
| Termination Reactions | 0.470 | 0.357 | 3.76 | 15.9 |
| Final Sample | 0.282 | 0.238 | 2.26 | 9.85 |
| Amount of Glycerol Loaded on Typical Electrophoresis Gel Lane (3 μl) | | | | |
| μl Glycerol per lane | 0.008 | 0.007 | 0.068 | 0.295 |
| μg Glycerol per lane | 10.7 | 9.00 | 85.3 | 372 |

Appropriate gel buffers can be determined by routine experimentation to find those which are useful in DNA separations and yet do not complex with glycerol or various sugars to form a distorting complex. For example, for the acid component weak acids can be used, including the following acids, which serve to replace boric acid in DNA sequencing gels: acetic acid, carbonic acid, glycine, serine, taurine, tricine (N-tris (hydroxyethyl) methylglycine), and bicine (N, N-bis(2-hydroxyethyl)glycine). Of these, the stronger acids (acetic and carbonic) yield buffers with higher conductivity than desired for routine use. The weakest acid, glycine, yields a buffer with a pH somewhat higher than normally used, although results are acceptable. The others all yield buffers with electrophoretic properties essentially identical to those of borate-containing buffers, but the addition of high concentrations of glycerol has no effect on the gel resolution. Glycine and taurine are preferred at present since they are less expensive than some of the other acids, and more soluble than D,L-serine. Other organic and inorganic acids could also be used, particularly those with a pKa value between 7 and 10 at 40°–50° C. For example, TAPS (3-[N-tris(hydroxymethyl) methyl-amino]-propanesulfonic acid), CHES (2-(N-cyclohexylamino) ethanesulfonic acid), AMPSO (3-[dimethyl (hydroxymethyl)-methylamino]-2-hydroxypropanesulfonic acid), CAPSO (3-(cyclohexylamino)-2-hydroxy-1-propanesulfonic acid), CAPS (3-N(Cyclohexylamino)-propanesulfonic acid), Glycylglycine, Threonine, allo-Threonine, arginine, 2-aminoethyl sulfuric acid, and glutamic acid.

EXAMPLES

The following buffers have been prepared and tested for running DNA sequencing gels. Typically, they were used as follows:

1. Buffer was prepared in concentrated form (usually 10-fold concentrate) with the quantities of reagents shown in Table 2.

2. A sequencing gel was prepared by mixing 7.6 g acrylamide, 0.4 g N, N'-methylene bisacrylamide, 42 g urea, concentrated buffer and water to a final dissolved volume of 100 ml. The volume of concentrated buffer was usually 10 ml but varied in actual experiments. Actual volumes used are listed in Table 2. The mixture was dissolved by gentle stirring at room temperature (about 20° C.)

3. The mixture was filtered either through Whatman #1 filter paper or a 0.4 μm nitrocellulose filter. Gel molding plates, spacers and comb were assembled using tape and clamps by standard procedures. The gel apparatus used is a model STS 45 from IBI division of Kodak. Gels were approximately 42 cm high, 37 cm wide and 0.4 mm thick, run with a 64-well "sharkstooth" comb.

4. When ready, 1.0 ml of 10% ammonium persulfate and 25 μl of N,N,N',N'-tetramethylethylenediamine were added to the gel forming solution and the gel poured immediately. Gels were typically used within 2–3 hours of pouring but sometimes used after sitting overnight at room temperature.

5. Gels were loaded with sequencing reaction products, labeled with $^{35}$S prepared using the USB SEQUENASE® Version 2.0 DNA sequencing kit and M13mp18 DNA for template.

6. Running buffer (1000 ml) was prepared by diluting the same concentrated buffer by the same ratio as for preparing the gel. Thus, the same buffer was present in the upper and lower chambers and in the gel itself. Gels were run at constant power (60–70 watts) until the bromophenol blue dye reached the bottom, typically 2–3 hours. The voltage and current required to maintain 60–70 watts varied in accordance with the conductivity of the buffer. Gels prepared with buffers of high conductivity generally ran slower.

7. Gels and sequencing reactions were also prepared for running on the Applied Biosystems Model 373A automated DNA sequencing instrument according to the instructions of the instrument manufacturer except for the substitution of buffer. These gels also were free of glycerol-induced artifacts and gave normal sequencing results.

8. These buffers also work for running horizontal agarose gels for the separation of DNAs much like the currently popular TBE and TAE buffers.

TABLE 2

| Buffer | Weak acid used (pKa at 45° C.) | Composition: g/500 ml Buffer Concentrate | | | pH (1:10) | Conductivity (of a 1:10 dilution) $\mu$mho/cm | Dilution for Gel ml/100 ml of Gel |
|---|---|---|---|---|---|---|---|
| | | Weak Acid | Tris | $Na_2$ EDTA | | | |
| 1 (TBE) | Boric Acid (9.1) | 28 | 54 | 4.5 | 8.16 | 755 | 10 |
| 2 | Bicine (7.9) | 50 | 54 | 4.5 | 8.20 | 1000 | 6.67 |
| 3 | D,L-Serine (8.7) | 35 | 54 | 4.5 | 8.47 | 734 | 10 |
| 4 | Acetic Acid (4.8) | a | 54 | 4.5 | 8.10 | 1150 | 10 |
| 5 | Carbonic Acid (6.3) | b | 54 | 4.5 | 8.23 | 1070 | 10 |
| 6 | Glycine (9.3) | 50 | 54 | 4.5 | 8.53 | 700 | 10 |
| 7 | Glycine (9.3) | 33.75 | 20 | 4.5 | 8.45 | 435 | 15 |
| 8 | Glycine (9.3) | 80 | 108 | 9 | 8.6 | 1500 | 5 |
| 9 | Tricine (7.6) | 15 | 54 | 4.5 | 8.23 | 1075 | 6.67 |
| 10 | Taurine (8.6) | 10 | 54 | 4.5 | 8.85 | 560 | 10 |
| 11 | Taurine (8.6) | 18 | 54 | 4.5 | 8.65 | 750 | 10 |
| 12 | Taurine (8.6) | 20 | 54 | 4.5 | 8.70 | 800 | 10 |
| 13 | Taurine (8.6) | 25 | 54 | 4.5 | 8.60 | 890 | 10 |
| 14 | Taurine (8.6) | 35 | 54 | 4.5 | 8.45 | 950 | 10 | aAcetic acid was added until the pH of the concentrated buffer was 8.3. This required approximately 12 ml of acetic acid.
bThe solution of Tris and EDTA was bubbled with $CO_2$ until the pH of the concentrated buffer was 8.3.

EXAMPLE 1

Figure 1:
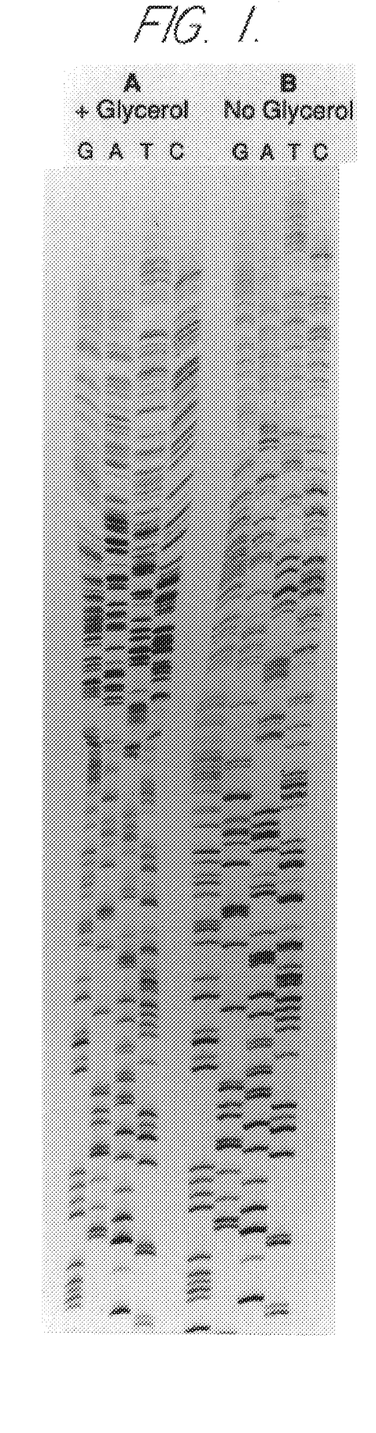
FIG. 1 is a reproduction of an autoradiogram of a DNA sequencing gel formed in the presence of a borate buffer showing that glycerol causes gel distortions.

Referring to FIG. 1, the gel picture demonstrates that glycerol causes sequencing gel distortions. One set of four DNA sequencing reactions was run using the SEQUENASE® Version 2.0 DNA sequencing kit (USB) using M13mp18 template DNA and $\alpha$-$^{35}$S dATP following the methods supplied with the kit. The final reaction products (G, A, T and C reactions, 10 $\mu$l each) were divided into two equal portions and 1 $\mu$l of 50% glycerol was added to one portion, resulting in a total glycerol concentration of about 8.6%. A 3 $\mu$l portion of these were loaded onto an 8% polyacrylamide sequencing gel prepared with normal TBE buffer. The four left-hand lanes contained the added glycerol such that 0.26 $\mu$l or 324 $\mu$g of glycerol was loaded into each lane. The distortion in these lanes is so severe that it also distorted the four adjacent lanes which carried the samples without added glycerol (total glycerol concentration about 0.28% so that a total of 0.0085 $\mu$l or 10.7 $\mu$g glycerol was loaded onto each lane). Other experiments have shown that while samples containing this amount of glycerol are essentially free of distortion, ones with twice this amount and above exhibit distortions which can interfere with readability of the gel.

EXAMPLE 2

Figure 2:
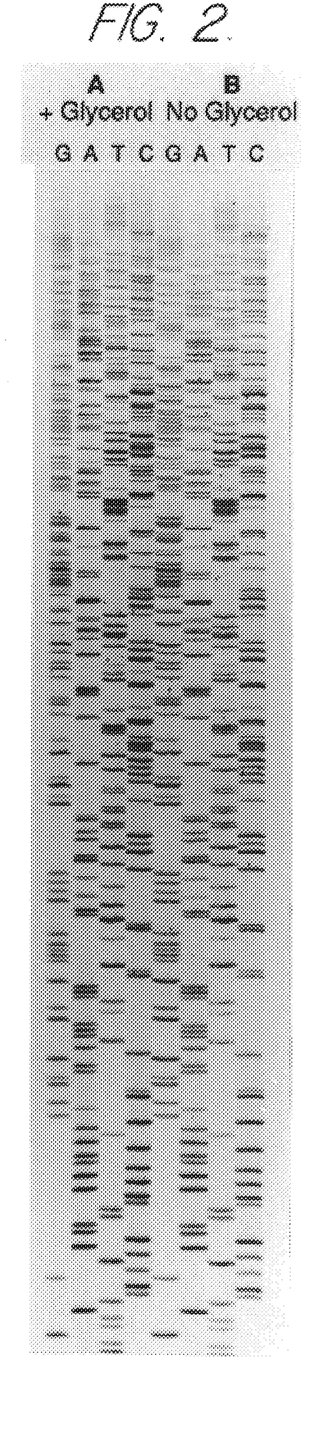
FIG. 2 is a reproduction of an autoradiogram of a DNA sequencing gel formed in the absence of a borate buffer showing that glycerol causes no distortion on a gel made using a glycerol-tolerant buffer.

Referring to FIG. 2, the gel picture demonstrates that glycerol causes no distortion on a gel made using a glycerol-tolerant buffer. Samples were prepared identically with those discussed above in Example 2, and were run on an 8% polyacrylamide gel using a buffer which contained taurine in place of boric acid. This buffer has the composition and properties of buffer 11 in Table 2. There is no evidence of any distortion even with this very high concentration of glycerol.

EXAMPLE 3

Figure 3A:
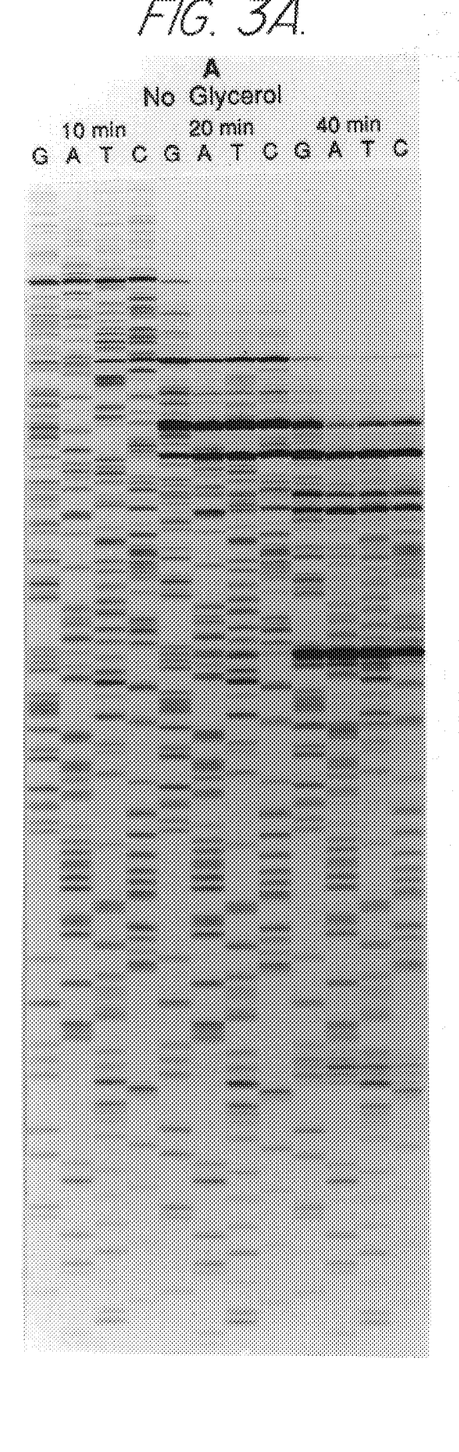
FIGS. 3A and B are reproductions of autoradiograms of a DNA sequencing gel in which DNA sequencing reactions are run in the absence or presence of glycerol.
Figure 3B:
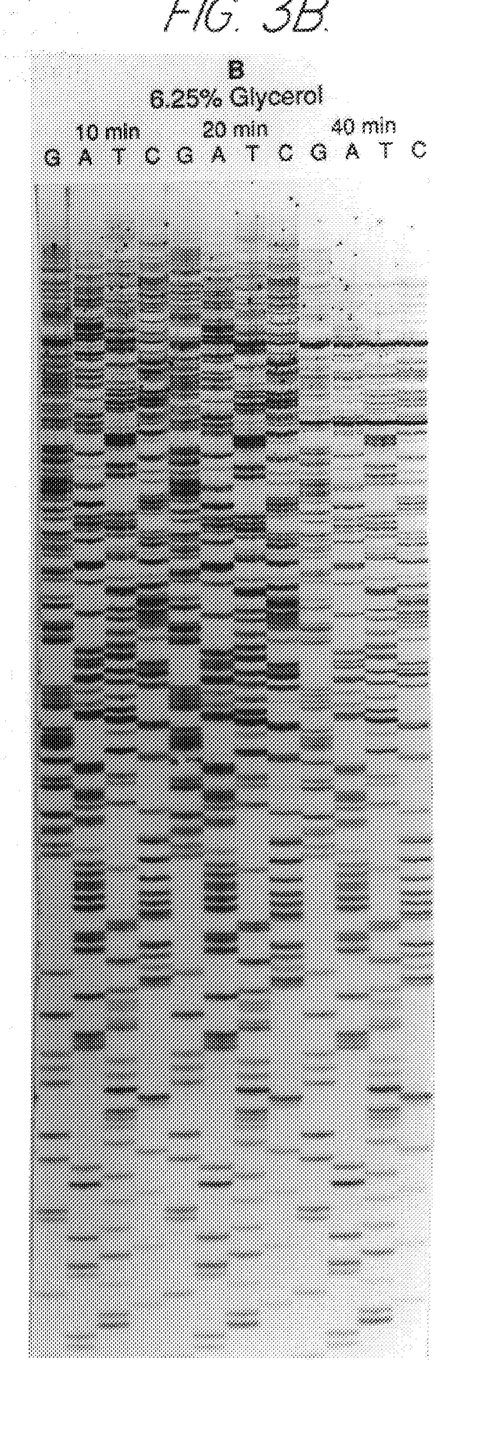

Referring to FIGS. 3A and 3B, the gel pictures demonstrate that DNA sequencing results can be improved if the reactions are run with added glycerol. Sequencing reactions were run as described in Example 1 except that the labeling step was run at 41° C. for 10, 20 or 40 minutes as indicated. In FIG. 3A, the enzyme was diluted normally so that the concentration of glycerol present during the labelling step was 0.8%. In FIG. 3B the enzyme was diluted using dilution buffer that contained 50% glycerol so that the concentration of glycerol present during the labelling step was 6.25%. The gel was identical to the one described in FIG. 2. Under these conditions, sequencing reactions run poorly with low glycerol concentration but the performance was restored when sufficient glycerol was added. If these sequences had been run on a normal TBE gel, severe distortions would have been evident.

EXAMPLE 4

Figure 4:
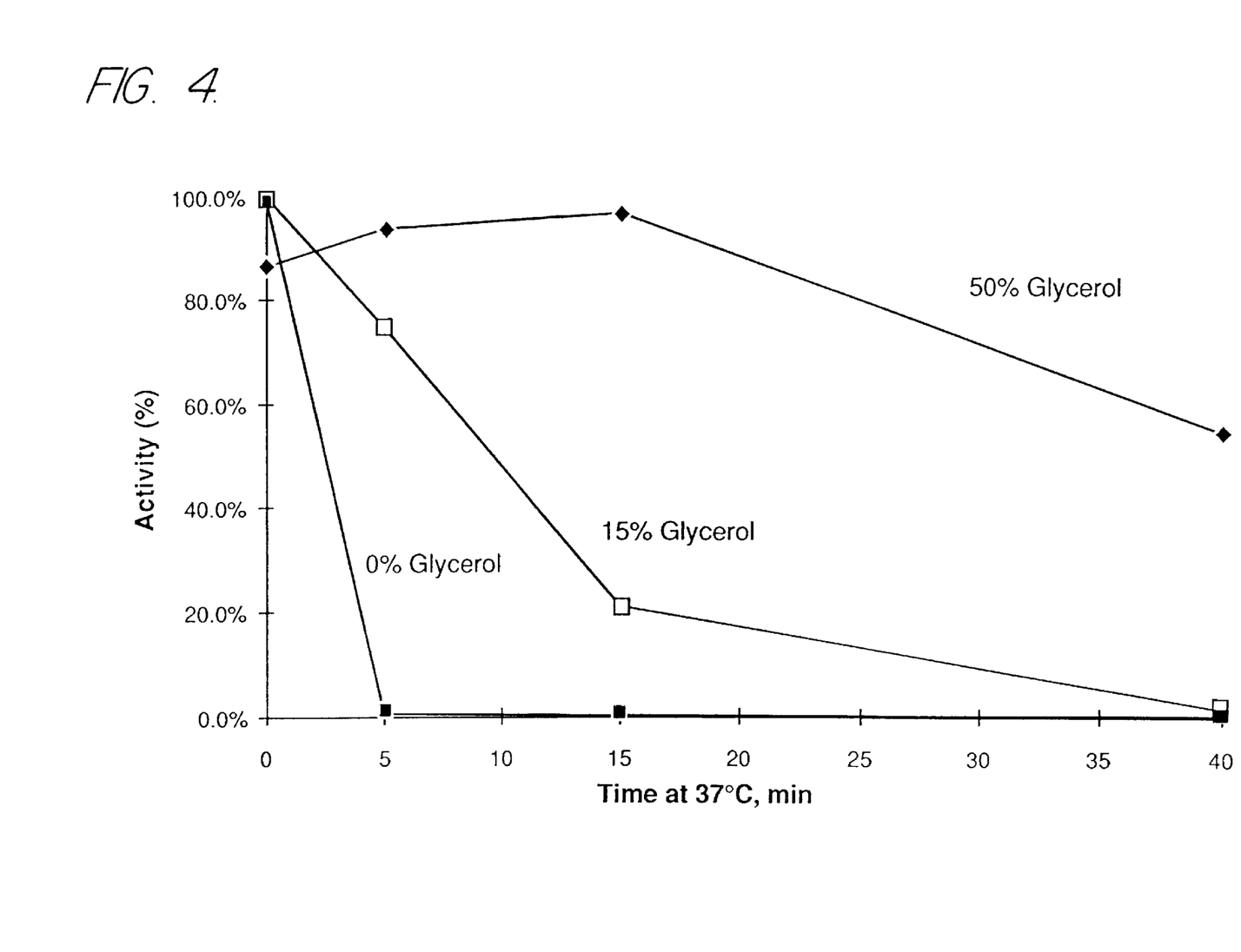
FIG. 4 is a graphical representation showing that glycerol stabilizes the activity of a T7 DNA polymerase.

Referring to FIG. 4, the graph demonstrates that glycerol stabilizes the activity of a modified T7 DNA polymerase. Samples of SEQUENASE Version 2.0 T7 DNA polymerase at a concentration of 0.5 Units/$\mu$l were incubated at 37° C. for the times indicated in 10 mM Tris-HCl (pH 7.5), 5 mM DTT and 0.5 mg/ml bovine serum albumin containing either no added glycerol, 15% glycerol or 50% glycerol as indicated. After incubation at 37° C., the samples were chilled on ice and assayed by a standard procedure. Assay reaction mixtures (100 $\mu$l) contained 40 mM Tris-HCl pH 7.5, 10 mM $MgCl_2$, 5 mM DTT, 0.3 mM dGTP, dCTP, DATP and [$^3$H]dTTP, 5 $\mu$g of M13mp18 single-stranded DNA pre-annealed to 5 pmol universal (−20) primer and enzyme. The enzyme (10 $\mu$l) was added last to the prewarmed (37° C.) reaction mixture and incubation was for 1 minute at 37° C. The reaction was stopped by the addition of 20 $\mu$l of 5 mg/ml fish-sperm DNA and 3 ml of 1N HCl, 0.1 M sodium pyrophosphate and acid-insoluble radioactivity determined by filtration using glass-fiber filters. Enzyme incubated in the absence of glycerol was inactivated within 5 minutes under these conditions but remained at least 50% active even after 40 minutes in the presence of 50% glycerol.

EXAMPLE 5

Buffers without EDTA

Buffers without EDTA present in them are particularly useful in this invention, e.g., buffers containing 40 g glycine, 54 g Tris in 500 ml, pH 8.6 and having a conductivity of 500 μmho/cm, can be used at a 1:10 dilution. Without EDTA bands at the bottom of gels are improved in separation and clarity.

EXAMPLE 6

Increasing Labeling Reaction Stringency

Another advantage of the ability to use glycerol to store a DNA polymerase prior to use in sequencing capitalizes on the increased thermal stability of some DNA polymerases in the presence of high concentrations of glycerol. For example, genetically modified T7 DNA polymerase (SEQUENASE VERSION 2.0 DNA polymerase) is much more stable at 37° C. in the presence of 15–50% glycerol. Since this enzyme is used at temperatures of 37° C. for sequencing (or higher, see below), improved stability at this temperature may improve sequencing results, as well as make sequencing more convenient.

That is, there is a benefit from the ability to add glycerol to DNA sequencing reactions in that the reactions can be run for longer periods of time and at warmer temperatures with less concern for polymerase stability. The original two-step sequencing protocol for sequencing with modified T7 DNA polymerase called for incubating the first (labeling) step for up to 5 minutes at about 20° C. (room temperature) or cooler. Incubations much warmer than this have previously resulted in severe sequencing problems. If the labeling step is performed at 41° C. after even brief incubations, a distinct pattern of artifact bands appears, which is probably the result of enzyme inactivation. However, if the polymerase is prediluted in a 50% glycerol-containing storage buffer, the sequences obtained with a 41° C. labeling step are good, even with labeling reaction times as long as 40 minutes. This allows more convenient sequencing protocols since the reactions can be run without strict attention to either incubation time or temperature.

Figure 5:
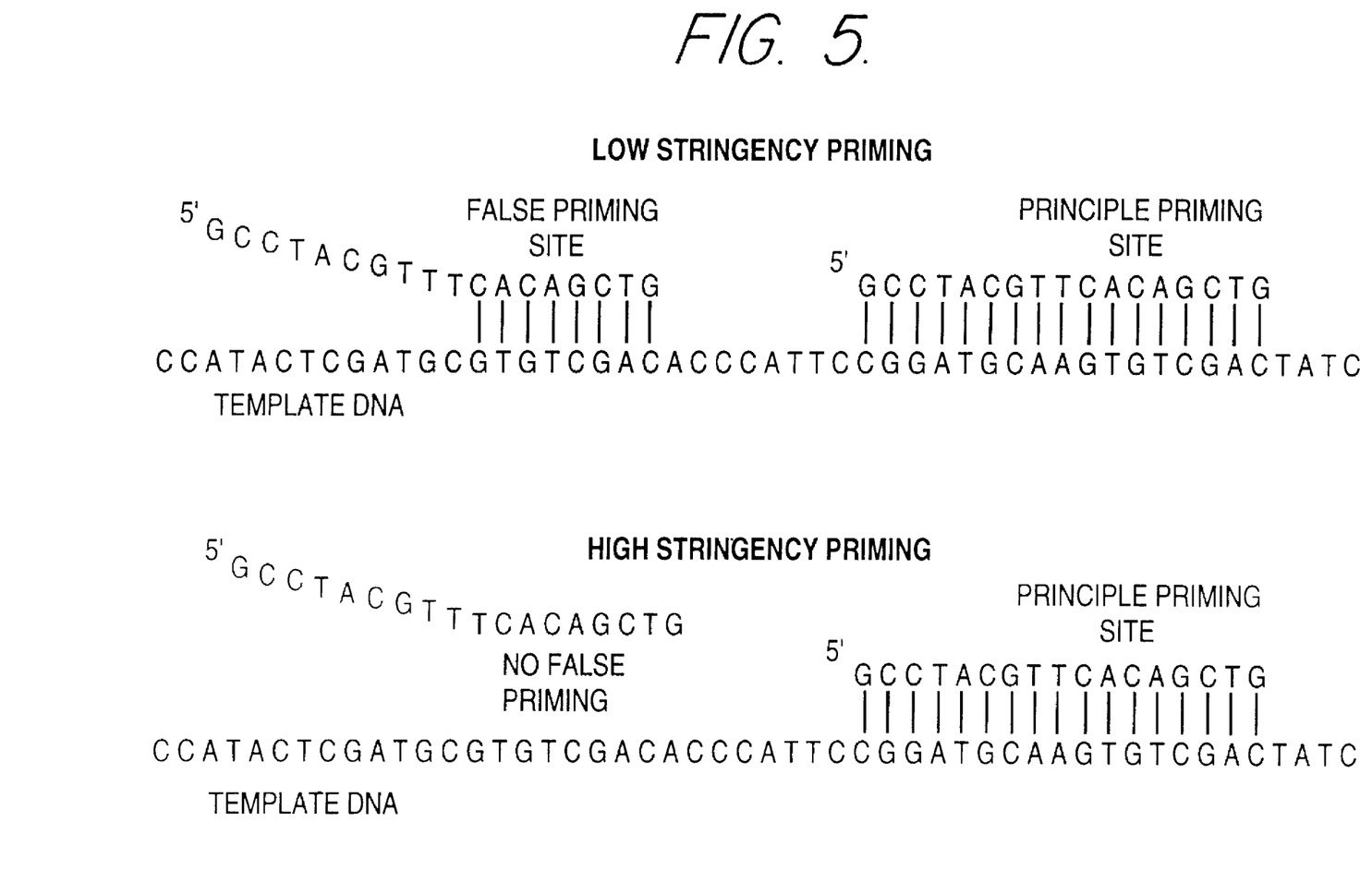
FIG. 5 is a diagrammatic representation of multiple binding sites on a DNA to be sequenced.

More important is the effect temperature can have on the overall performance of sequencing reactions. Chain-termination sequencing requires the use of a short primer (usually a synthetic oligonucleotide) to initiate synthesis of DNA. While efforts may be taken to ensure that his oligonucleotide primes synthesis at a unique site in the template DNA, it is never entirely feasible to eliminate the possibility of multiple priming sites when determining new sequence. As shown in FIG. 5, even a few nucleotides, if at the 3' end of the primer, might effectively prime synthesis at an unintended site.

When using a two-step protocol, the primer itself is directly extended during the labeling step. It is in this step that primer specificity or lack of specificity is important. During this step, the primer is extended until the supply of nucleotide is exhausted, typically an average of 20–50 nucleotides. If this step is run under low temperature conditions (low stringency), the priming may occur not only at the intended, 100% matching site, but also at sites where fewer bases match at the 3' terminus of the primer, perhaps as few as 5–7 nucleotides. Priming at these sites will be exhibited as a second sequence along with the sequence from the 100% matched site. This secondary sequence may be fainter than the primary one, especially if a large excess of primer is avoided, but it may well make reading the primary sequence difficult or impossible. If the temperature (stringency) of the labeling reaction can be increased, priming at the secondary site may be eliminated, making the particular primer/template combination usable.

Figure 6:
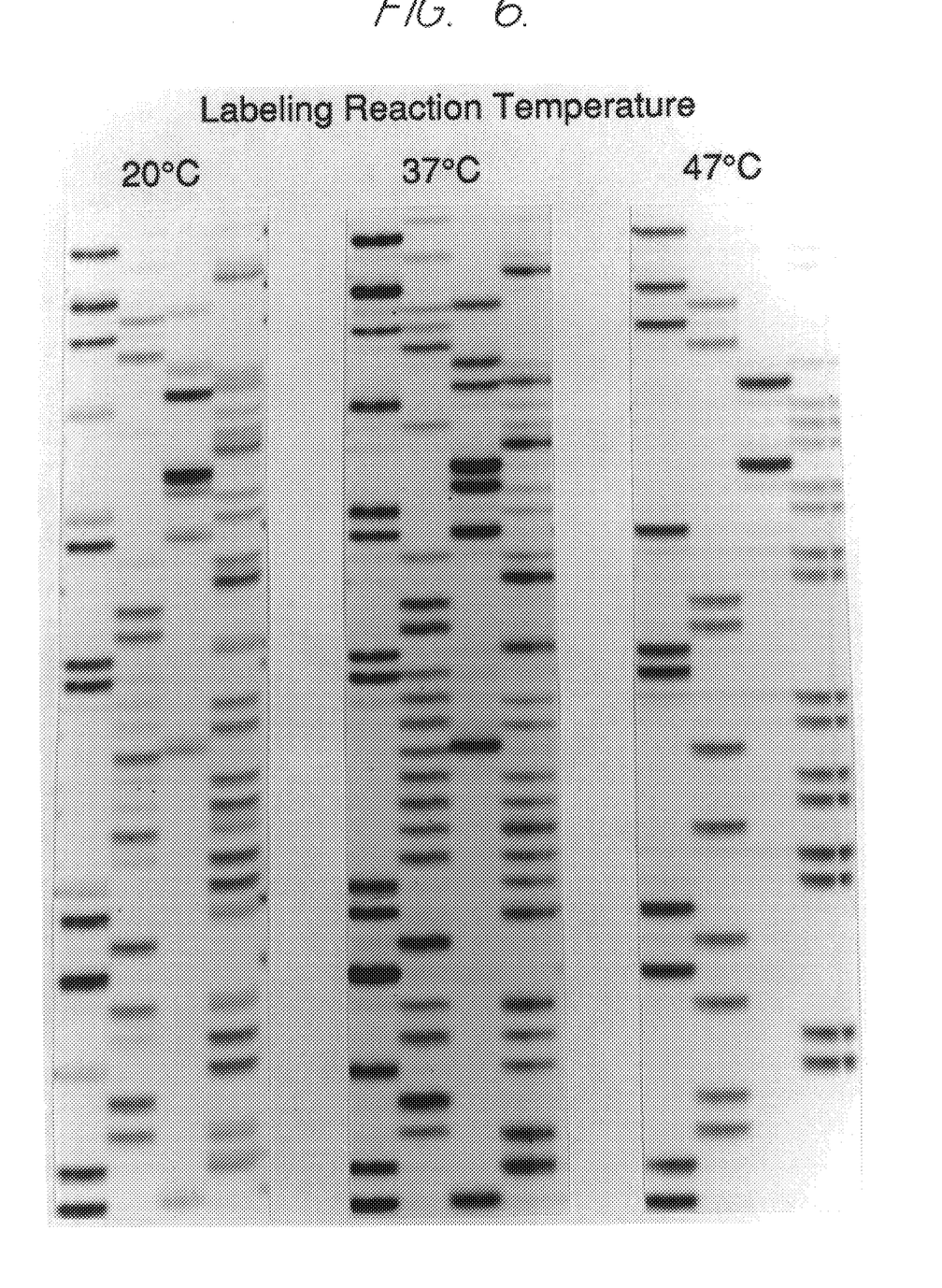
FIG. 6 is a reproduction of an autoradiogram of a DNA sequencing gel showing the advantage of use of a high temperature for a labelling reaction in a DNA sequencing procedure.

An example of low-stringency priming of a mismatched primer is shown in FIG. 6. In one experiment, when the labeling step was run at low temperature, a double sequence is obtained, one from the primary (matched) site and one from the secondary (10-base) site. When the temperature of the labeling reaction was raised to 47° C., unique sequence was obtained, indicating that the primer only anneals at its primary site at this elevated temperature.

Specifically, a series of identical sequencing reactions (with $Mn^{2+}$) were run, varying only the temperature of the labeling reaction. The template was M13mp18 single-stranded DNA and the primer was an 18-mer with the sequence 5'-TTTTCATCGGCATTTTCG (SEQ ID NO.:1. It matches the sequence of single-stranded M13mp18 at position 2464–2447 and the 10-nucleotide sequence at its 3' end also matches the same template at position 3703–3694. Thus, double-priming of the type depicted in FIG. 5 may occur with this primer when sequencing (labeling) reactions are run at low stringency, but may not occur when stringency is high enough. Labeling reactions were run using a 5:1 primer: template mole ratio with pre-warming of the reaction mixture at the indicated temperature prior to adding polymerase. Incubation was continued for 5 minutes and termination reactions were run at 37° C. for 5 minutes. The sequences run using 20° C. and even 37° C. labeling steps have distinct patterns of multiple priming events. The sequence run using a 47° C. labeling step is essentially free of double priming. Similar results were obtained in the absence of $Mn^{2+}$. Thus, primers which may be too nonspecific to use under low stringency conditions may be specific and usable under more stringent conditions.

EXAMPLE 7

Increasing Termination Reaction Temperature

There may also be some reason to prefer running the termination reactions at elevated temperatures as well. Polymerizations will be more rapid at the elevated temperatures, and some template secondary structures may be eliminated at temperatures above 50° C. Sequences of single- and double-stranded template DNAs can be obtained with termination reaction temperatures up to 70° C. with T7 DNA polymerase. These termination reaction temperatures are made reliable by the addition of glycerol to the reaction mixture. (See FIG. 7)

Figure 7:
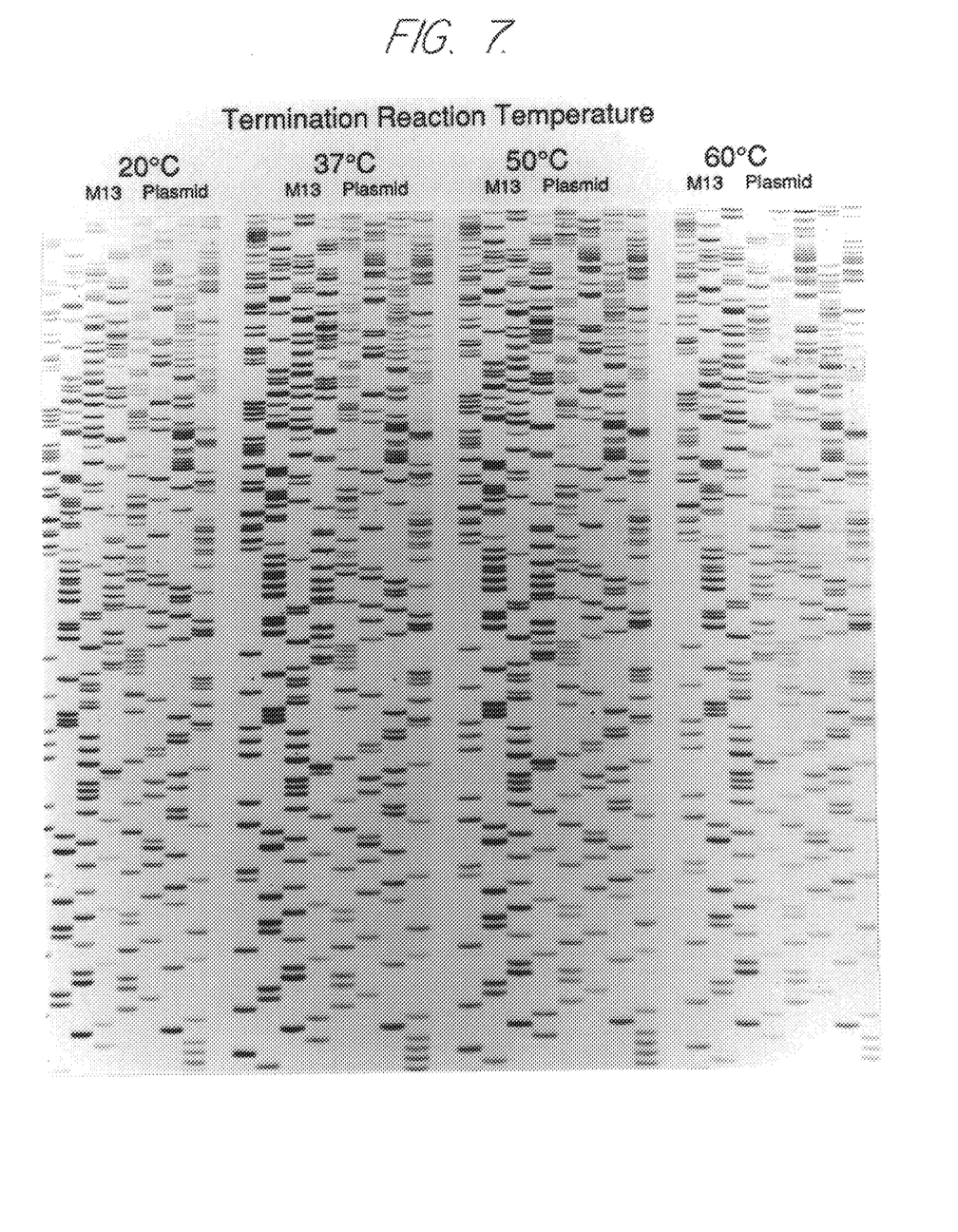
FIG. 7 is a reproduction of an autoradiogram of a DNA sequencing gel showing the ability to use high temperatures for termination reactions in a DNA sequencing procedure.

Referring to FIG. 7, sequencing reactions were run using a 96-well plate format kit (described in example 8) so that the termination reactions contained 20% glycerol. Labeling reactions were done at 20° C., termination reactions were pre-warmed at the indicated temperatures. Template was either M13mp18(M13) or alkali-denatured BLUESCRIPT (Plasmid). Note that there is little difference in performance using termination reaction temperatures from 20° C. to 60° C. Higher temperatures should improve performance when templates with strong secondary structures are used.

There are yet other situations where it is more convenient to tolerate glycerol in DNA sequencing samples. For instance, one way to sequence large linear DNAs is to cut them with a restriction enzyme and gene 6 exonuclease. Both of these enzymes are typically supplied in 50% glycerol, so the glycerol content of the template and subsequent sequencing reactions is increased.

In these and perhaps many other situations, it is important to have sequencing gels available which can tolerate loading of glycerol along with the DNA sample. This can be readily and inexpensively achieved by changing the buffer in the sequencing gel to one which does not react with glycerol. This opens up many new possibilities for making sequencing reactions both more convenient and more reliable.

Kits

SEQUENASE and TAQUENCE kits presently require dilution of enzyme 8-fold prior to use. The present invention allows production of a kit in which the reagents are re-formulated to contain enzyme at ⅛th the normal concentration in a 50%-glycerol solution so that the kit enzyme can be used directly without dilution. Such a kit will save the user time, and possibly allow the user more actual sequences per kit and more flexible use of the enzyme in situations where only 1 or 2 sequences are being performed on a given day. Since the sequencing reaction products will contain large quantities of glycerol, a glycerol-tolerant gel formulation of this invention, or the extra work of removing glycerol from the products will be required.

A new kit can also be produced, perhaps in a 96-well plate format, which consists of pre-dispensed reagents for sequencing. The enzyme can be dispensed at its final working concentration in 50% glycerol buffer, in which it is stable even for a 15–20 minute incubation at 37° C. Other reaction components whose volumes are critical can also be dispensed using 30–50% glycerol which prevents the component from freezing under the plate storage condition (−20° C.) and prevents loss by evaporation (or lyophilization) which occurs when covered plates are frozen. Components whose volume are not critical can simply be dispensed in the plate in convenient amounts. A possible configuration is as follows:

|              | 1 | 2 | 3 | 4 | 5 | 6 | 7 | 8 | 9 | 10 | 11 | 12 |
|--------------|---|---|---|---|---|---|---|---|---|----|----|----|
| Enzyme       | ○ | ○ | ○ | ○ | ○ | ○ | ○ | ○ | ○ | ○  | ○  | ○  |
| Labeling Mix | ○ | ○ | ○ | ○ | ○ | ○ | ○ | ○ | ○ | ○  | ○  | ○  |
| Stop Solution| ○ | ○ | ○ | ○ | ○ | ○ | ○ | ○ | ○ | ○  | ○  | ○  |
| Buffer       | ○ | ○ | ○ | ○ | ○ | ○ | ○ | ○ | ○ | ○  | ○  | ○  |
| ddGTP Mix    | ○ | ○ | ○ | ○ | ○ | ○ | ○ | ○ | ○ | ○  | ○  | ○  |
| ddATP Mix    | ○ | ○ | ○ | ○ | ○ | ○ | ○ | ○ | ○ | ○  | ○  | ○  |
| ddTTP Mix    | ○ | ○ | ○ | ○ | ○ | ○ | ○ | ○ | ○ | ○  | ○  | ○  |
| ddCTP Mix    | ○ | ○ | ○ | ○ | ○ | ○ | ○ | ○ | ○ | ○  | ○  | ○  |

The template DNA and primer are added to the buffer well and the entire plate incubated at 37° C. for 10 minutes to anneal. Then the labelled nucleotide, labeling mix and enzyme are added to the buffer well and the labeling step incubated for about 5 minutes at room temperature. The temperature of the plate is increased to 37° C. and one quarter of the mixture then transferred to each of the ddNTP mixes in the lower wells for the termination step (at least 5 minutes). Finally, stop solution is transferred from its well to the termination reactions. Since the timing of the steps is not critical, up to 12 templates can be sequenced at once. When fewer templates are to be sequenced, an appropriate area of the plate can simply be cut with scissors and used.

For automated pipetting devices, it is critical that the final total volume of the labeling reaction be known, so evaporation or condensation of the buffer, enzyme and labeling mix during cold storage must be minimized. This can be accomplished by the addition of 30–50% glycerol or ethylene glycol which prevents freezing and evaporation or lyophilization. Since the sequencing reaction products will contain large quantities of glycerol, a glycerol-tolerant gel formulation or the extra work of removing glycerol from the products will be required.

EXAMPLE 8

SEQUENASE DNA Sequencing Plate Kit

This plate-format kit is designed to run 12 sequences at a time. All of the reagents required except template DNA, primer, and radioactive nucleotide are contained on the plate. The plates include reagents for sequencing with 7-deaza-dGTP to eliminate compression artifacts.

High concentrations of glycerol are used to preserve the enzyme activity and the volumes of the labeling mixture and buffer. These high concentrations of glycerol would normally interfere with the sequencing gel, but the use of a new glycerol-tolerant sequencing gel buffer conveniently and inexpensively eliminates this problem.

The plate is prepared in 12 columns of 8 different reagents (see above). Each column is sufficient for one DNA sequence. The compositions and volumes of each of the reagents is given below. The enzyme is given a light blue color and the labeling mixture a light red color with dyes. These help to visually verify the actions of the program. The Stop Solution is dark blue since it contains electrophoresis tracking dyes.

The protocol is as follows:

1. Prepare 12 template DNA samples (13 μl). These must contain approximately 1 μg of M13 or 3–5 μg of denatured plasmid DNA in 13 μl of TE buffer.
2. Add 1 μl primer to each DNA sample. The primer should be 0.5–5 pmol/μl concentration. The control "−40" M13 primer included is 0.5 pmol/μl.
3. Add 0.5 μl (5 μCi) of $^{35}$S DATP (~1000 Ci/mmol) to each DNA sample.
4. Remove a plate from the freezer, keeping it upright. Place it on the bench at room temperature and carefully remove the tape-like plastic cover. This cover may be saved for re-sealing the plate later.
5. Transfer the entire volume (14.5 μl) of each template/primer to individual buffer wells on the plate as illustrated.

|  | 1 | 2 | 3 | 4 | 5 | 6 | 7 | 8 | 9 | 10 | 11 | 12 |
|---|---|---|---|---|---|---|---|---|---|---|---|---|
| Enzyme | ○ | ○ | ○ | ○ | ○ | ○ | ○ | ○ | ○ | ○ | ○ | ○ |
| Labeling Mix | ○ | ○ | ○ | ○ | ○ | ○ | ○ | ○ | ○ | ○ | ○ | ○ |
| Stop solution | ○ | ○ | ○ | ○ | ○ | ○ | ○ | ○ | ○ | ○ | ○ | ○ |
| Buffer | ● | ● | ● | ● | ● | ● | ● | ● | ● | ● | ● | ● |
| ddGTP Mix | ○ | ○ | ○ | ○ | ○ | ○ | ○ | ○ | ○ | ○ | ○ | ○ |
| ddATP Mix | ○ | ○ | ○ | ○ | ○ | ○ | ○ | ○ | ○ | ○ | ○ | ○ |
| ddTTP Mix | ○ | ○ | ○ | ○ | ○ | ○ | ○ | ○ | ○ | ○ | ○ | ○ |
| ddCTP Mix | ○ | ○ | ○ | ○ | ○ | ○ | ○ | ○ | ○ | ○ | ○ | ○ |

12 template samples with primer and $^{35}S$ are placed in these wells.

6. Annealing: Incubate the entire plate at 37° C. for 10 minutes (optimally, the enzyme wells can be kept cooler by extending them off the surface of the heating block).
7. Cool on an ice block 1 minute.
8. Labeling Reaction: Transfer 5 μl of labeling mix (Red, row B) to the template well. Similarly transfer enzyme (Blue, row A) to the reaction well. Mix well. Place plate at room temperature 3–5 minutes.
9. Pre-warm entire plate on 37° C. block 1 minute.
10. Termination Reactions: Transfer 5 μl of labeling reaction to each of the termination wells (rows E-H), mix well. Incubate 5 minutes or longer at 37° C.
11. Stop: Transfer 5 μl of Stop Solution (dark Blue, row C) to each termination reaction, mix well.
12. Cover the plate with a tape sealer and store in the freezer if desired.
13. When the glycerol-tolerant sequencing gel is ready to load, uncover the plate and place it on top of a heating block set to 70°–80° C. to heat the samples. Heat 3–4 minutes, avoiding excessive evaporation. Load as soon as possible after heating.
14. Load the samples as sets of 4 adjacent lanes as illustrated.

The labeling and termination steps can be run at room temperature with no apparent difficulty. Annealing at room temperature (10 minutes) can be achieved using at least 2:1 primer:template mole ratio.

Plates can be readily cut with scissors for running fewer than 12 reactions.

Labeling reactions can be run as warm as 45° C. for up to 5 minutes. This may be useful for increasing the primer specificity in cases where the primer may anneal at more than one place. Termination reactions can be run at temperatures as high as 60° C. if the labelling reaction is maintained at room temperature. To do this, the termination wells are cut off the plate, and preincubated at the high temperature for a few seconds before addition of the labeling reaction mix.

Reagent Compositions:

| | | |
|---|---|---|
| 1. Enzyme | 5 µl | 0.65 Units/82 l Ver. 2.0 in 50% glycerol buffer (Bromcresol |

-continued

Reagent Compositions:

| | | |
|---|---|---|
| | | Green, 0.02%) |
| 2. Lab. Mix | 5 µl | 0.6 µM each 7-deaza-dGTP, dTTP, dCTP in 40% glycerol (Phenol Red, 0.02%) |
| 3. Stop Solution | 30 µl | 95% Formamide, 20 mM EDTA, 0.05% Bromophenol Blue, 0.05% Xylene Cyanol FF |
| 4. Buffer | 5 µl | 100 mM Tris (7.5), 50 mM $MgCl_2$, 125 mM NaCl, 40% glycerol. |
| 5. ddG | 5 µl | 50 mM NaCl, 40 µM each dNTP, 4 µM ddGTP, 20% Glycerol. |
| 6. ddA | 5 µl | 50 mM NaCl, 40 µM each dNTP, 4 µM ddATP, 20% Glycerol. |
| 7. ddT | 5 µl | 50 mM NaCl, 40 µM each dNTP, 4 µM ddTTP, 20% Glycerol. |
| 8. ddC | 5 µl | 50 mM NaCl, 40 µM each dNTP, 4 µM ddCTP, 20% Glycerol. |

Other embodiments are within the following claims.

I claim:

1. A method for electrophoresis, through a gel comprising polyacrylamide, of nucleic acid fragments present in a solution comprising an amount greater than or equal to 0.2% of a 1,2-diol comprising reagent which interacts with boric acid or borate and causes distortion of movement of a portion of said nucleic acid fragments comprising fragments of 400 to 600 nucleotides in length in a borate buffered gel, comprising the steps of:

applying said solution to a polyacrylamide electrophoretic gel and electrophoresing said fragments into said gel in the presence of a buffer lacking boric acid or borate or a derivative thereof which interacts with said reagent and thereby causes distortion of electrophoresis of a portion of said fragments comprising fragments of 400 to 600 nucleotides in length and in the absence of any buffer comprising said boric acid or said borate or said derivatives thereof.

2. A method for electrophoresis, through a gel comprising polyacrylamide, of nucleic acid fragments present in a solution comprising an amount greater than or equal to 0.2% glycerol, comprising the steps of:

applying said solution to a polyacrylamide electrophoretic gel and electrophoresing said fragments into said gel in the presence of a buffer lacking boric acid or borate or a derivative thereof which interacts with said glycerol and thereby causes distortion of electrophoresis of a portion of said fragments comprising fragments of 400 to 600 nucleotides in length and in the absence of any buffer comprising said boric acid or said borate or said derivatives thereof.

3. A method for electrophoresis, through a gel comprising polyacrylamide of nucleic acid fragments present in a solution comprising an amount greater than or equal to 0.2% dithiothreitol, comprising the steps of:

applying said solution to a polyacrylamide electrophoretic gel and electrophoresing said fragments into said gel in the presence of a buffer lacking boric acid or borate or a derivative thereof which interacts with said dithiothreitol and thereby causes distortion of electrophoresis of said fragments and in the absence of any buffer comprising said boric acid or said borate or said derivatives thereof.

4. A method for electrophoresis, through a gel comprising polyacrylamide, of nucleic acid fragments present in a solution comprising an amount greater than or equal to 0.2% trehalose, comprising the steps of:

applying said solution to a polyacrylamide electrophoretic gel and electrophoresing said fragments into said gel in the presence of a buffer lacking boric acid or borate or a derivative thereof which interacts with said trehalose and thereby causes distortion of electrophoresis of said fragments and in the absence of any buffer comprising said boric acid or said borate or said derivatives thereof.

5. A method for electrophoresis, through a gel comprising polyacrylamide, of nucleic acid fragments present in a solution comprising an amount greater than or equal to 0.2% ethylene glycol, comprising the steps of:

applying said solution to a polyacrylamide electrophoretic gel and electrophoresing said fragments into said gel in the presence of a buffer lacking boric acid or borate or a derivative thereof which interacts with said ethylene glycol and thereby causes distortion of electrophoresis of said fragments and in the absence of any buffer comprising said boric acid or said borate or said derivatives thereof.

6. The method of any of claims 1, 2, 3, 4, or 5, wherein said fragments are produced during an enzymatic DNA sequencing reaction.

7. The method of any of claims 1, 2, 3, 4, or 5, wherein said gel is a DNA sequencing gel.

8. The method of claim 6 wherein said reaction is performed in the presence of said glycerol.

9. The method of any of claims 1 or 2 wherein said buffer comprises an acid portion chosen from acetic acid, carbonic acid, glycine, serine, taurine, tricine, and bicine.

10. The method of any of claims 1 or 2 wherein said buffer lacks EDTA.

11. A method for sequencing DNA comprising the steps of performing an enzymatic dideoxy DNA sequencing reaction in the presence of at least 15 glycerol and a thermolabile DNA polymerase at a temperature of 60° C. or above.

12. The method of claim 11 wherein said DNA polymerase is a T7 DNA polymerase.

13. The method of any of claims 3, 4 or 5 wherein said buffer comprises an acid portion chosen from acetic acid, carbonic acid, glycine, serine, taurine, tricine, and bicine.

14. A method for electrophoresis, through a gel comprising polyacrylamide, of nucleic acid fragments present in a solution comprising an amount greater than or equal to 0.2% glycerol, comprising the steps of:

applying said solution to a polyacrylamide electrophoretic gel and electrophoresing said fragments into said gel in the presence of a buffer lacking boric acid or borate or a derivative thereof which interacts with said glycerol and thereby causes distortion of electrophoresis of said fragments and in the absence of any buffer comprising said boric acid or said borate or said derivatives thereof; wherein said buffer comprises an acid portion chosen from acetic acid, carbonic acid, glycine, serine, taurine, tricine, and bicine.

15. The method of any of claims 3, 4 or 5 wherein said buffer lacks EDTA.

16. A method for electrophoresis, through a gel comprising polyacrylamide, of nucleic acid fragments present in a solution comprising an amount greater than or equal to 0.2% glycerol, comprising the steps of:

applying said solution to a polyacrylamide electrophoretic gel and electrophoresing said fragments into said gel in the presence of a buffer lacking boric acid or borate or a derivative thereof which interacts with said glycerol and thereby causes distortion of electrophoresis of said fragments and in the absence of any buffer comprising said boric acid or said borate or said derivatives thereof; wherein said buffer lacks EDTA.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 1:

TTTTCATCGG CATTTTCG            18

( 2 ) INFORMATION FOR SEQ ID NO: 2:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear     ( i i ) SEQUENCE DESCRIPTION: SEQ ID NO: 2:

GCCTACGTTC ACAGCTG            17

( 2 ) INFORMATION FOR SEQ ID NO: 3:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear     ( i i ) SEQUENCE DESCRIPTION: SEQ ID NO: 3:

GCCTACGTTC ACAGCTG            17

( 2 ) INFORMATION FOR SEQ ID NO: 4:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear     ( i i ) SEQUENCE DESCRIPTION: SEQ ID NO: 4:

CCATACTCGA TGCGTGTCGA CACCCATTCC GGATGCAAGT GTCGACTATC            50

( 2 ) INFORMATION FOR SEQ ID NO: 5:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear     ( i i ) SEQUENCE DESCRIPTION: SEQ ID NO: 5:

GCCTACGTTC ACAGCTG            17

( 2 ) INFORMATION FOR SEQ ID NO: 6:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear     ( i i ) SEQUENCE DESCRIPTION: SEQ ID NO: 6:

GCCTACGTTC ACAGCTG            17

( 2 ) INFORMATION FOR SEQ ID NO: 7:

( i ) SEQUENCE CHARACTERISTICS:
        ( A ) LENGTH: 50
        ( B ) TYPE: nucleic acid -continued (C) STRANDEDNESS: single
(D) TOPOLOGY: linear (i i) SEQUENCE DESCRIPTION: SEQ ID NO: 7:

CCATACTCGA TGCGTGTCGA CACCCATTCC GGATGCAAGT GTCGACTATC         50